United States Patent [19]
Garvin

[11] Patent Number: 5,984,898
[45] Date of Patent: Nov. 16, 1999

[54] RETRACTABLE NEEDLE AND SYRINGE COMBINATION

[75] Inventor: David M. Garvin, Miami, Fla.

[73] Assignee: Retrax Safety Systems Inc., Miami, Fla.

[21] Appl. No.: 09/250,613

[22] Filed: Feb. 17, 1999

[51] Int. Cl.[6] .................................................. A61M 5/00
[52] U.S. Cl. ............................................ 604/195; 604/110
[58] Field of Search .................................... 604/195, 263, 604/192, 198, 110, 187, 218

[56] References Cited

U.S. PATENT DOCUMENTS

| | | | |
|---|---|---|---|
| 4,838,863 | 6/1989 | Allard et al. | 604/110 |
| 4,838,869 | 6/1989 | Allard et al. | 604/195 |
| 5,201,710 | 4/1993 | Caselli | 604/195 X |
| 5,407,436 | 4/1995 | Toft et al. | 604/195 |

Primary Examiner—John D. Yasko
Attorney, Agent, or Firm—Liniak, Berenato, Longacre & White

[57] ABSTRACT

A combination syringe and needle are disclosed wherein the needle assembly is mounted to a retractable element which retracts into the body of the syringe plunger. The needle assembly is mounted to the needle retractor which is spring biased to retract the needle. The retraction is actuated by releasing the forward end of the retractors from engagement with a collet positioned within the forward end of the syringe outer barrel. The collet is configured so as to clamp the forward end of the retractor and only releases the forward end when the collet is pushed forward, expanded, and disengages the forward end of the needle retractor. The pressure required to fully expand the collet causes the cap located on the forward end of the hollow plunger to collapse after being penetrated by puncture tabs formed on the collet base. The hollow plunger serves as a receptive container for the needle and hub forced into the syringe by spring biased upon release of the holder by the collet as it expands.

10 Claims, 5 Drawing Sheets

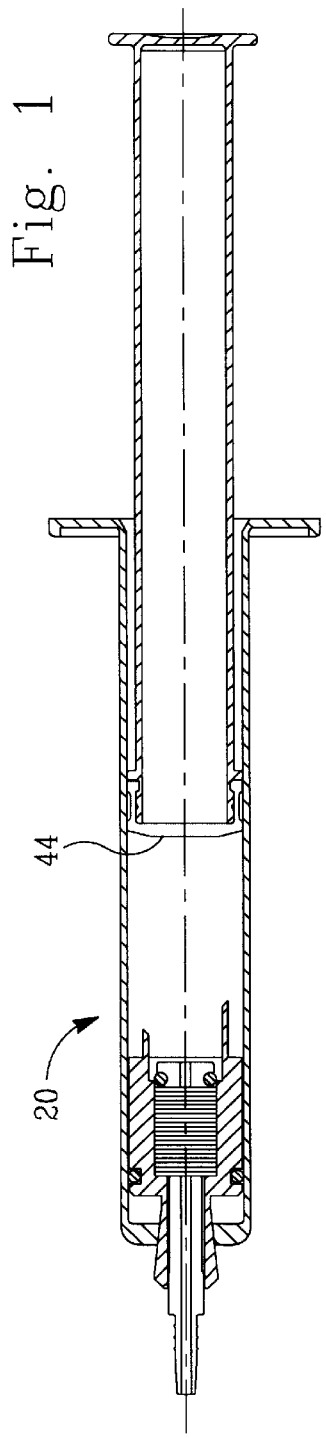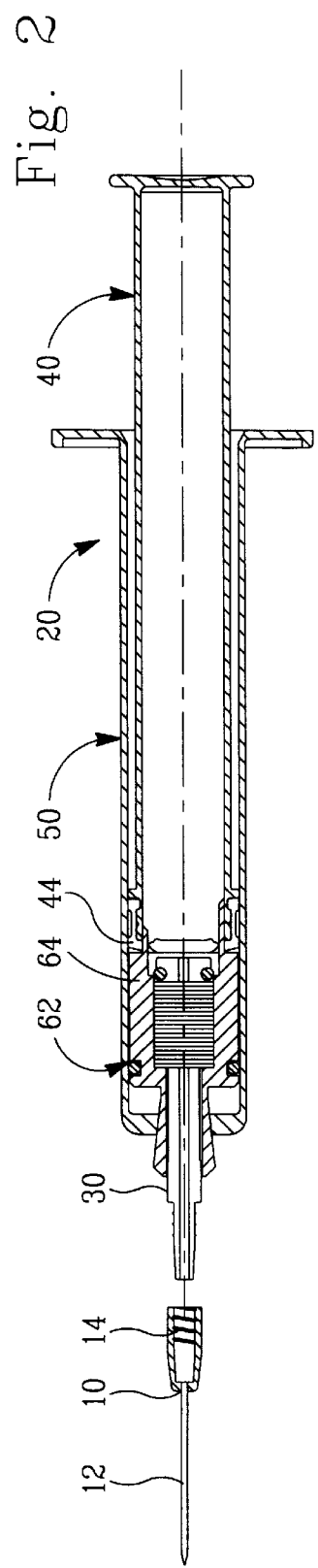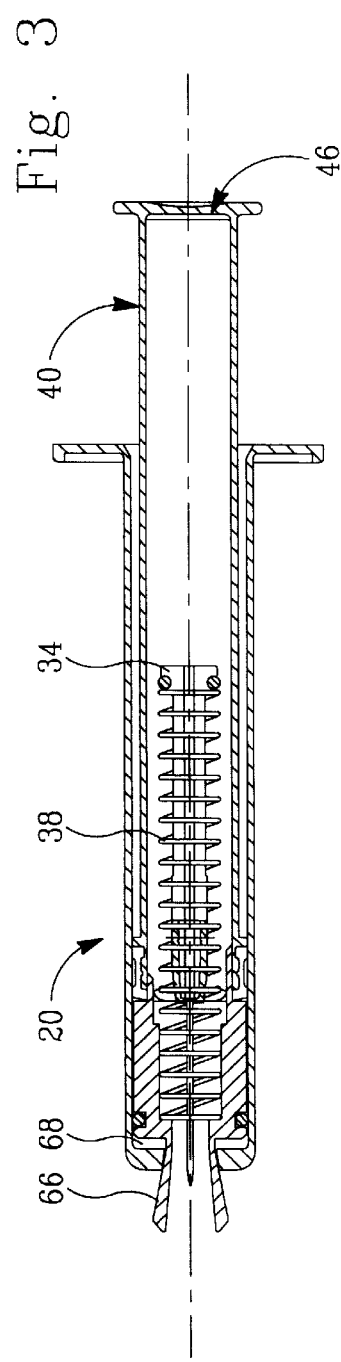

RETRACTABLE NEEDLE AND SYRINGE COMBINATION

FIELD OF THE INVENTION

The invention relates to medical syringes including needles. The invention will permit the production of a cost effective safety medical syringe which, following use, will prevent needle sticks to the medical worker. More specifically, the invention relates to a combination device including a retractable needle and syringe which, following a full stroke of the syringe plunger, automatically retracts the needle into the body of the syringe thereby preventing the possibility of needle sticks. Since the identification of the needle stick as a significant risk to the health and well being of medical workers owing to the transfer of blood borne diseases, many devices have been proposed to eliminate or reduce this risk. While these devices have been theoretically manufacturable, from a practical standpoint the vast majority of the devices incorporated designs and technology that did not lend to mass production and/or economically feasible production. The problems associated with prior devices have included simply being too sophisticated to employing technology and techniques, for example molding tolerances, which could not be adapted to mass and/or economically feasible production.

Examples of prior art solutions to these problems abound in the art. U.S. Pat. No. 5,324,265 is one example of the prior art wherein the device relies on many separate seals and spring action to overcome the seal to retract the needle into a central portion of the plunger. The device also uses a special needle, assembly and forward plug arrangement for the outer portion of the syringe.

U.S. Pat. No. 5,385,551 discloses a syringe including a retractable needle which relies on a removable plug at the forward end of the plunger. The plug is displaced by the force of a spring carrying the needle into the body of the plunger. This device requires several specialized subassemblies to operate, including a specialized needle assembly.

U.S. Pat. No. 5,389,076 also discloses a combination syringe and retractable needle assembly. This device relies on the displacement of a forward ring seal along the length of the needle holder, whereby the needle holder is released rearwardly into the body of the plunger. This device also requires a specialized needle holder.

U.S. Pat. No. 5,395,337 discloses a combination syringe and needle similar in construction to the already mentioned U.S. Pat. No. 5,324,265 in that the device relies on spring action to break seal resistance and retract the needle into the body of the plunger. Many specialized components are necessary for use and assembly.

U.S. Pat. No. 5,407,431 also discloses a retractable needle and syringe type device (in this case a catheter insertion device) This device relies on a spreading collar surrounding a needle holder which, upon being spread by the forward movement of the plunger leading end, uses a spring loaded forward of the needle to push the needle into the plunger. Many specialized parts are required for assembly and use.

U.S. Pat. No. 5,407,436 discloses a retractable needle and syringe combination which relies on the forward push of the plunger to disengage the needle holder and send it, by spring action, rearwardly into the body of the syringe. The spring action must breach a seal in the central portion of the plunger and propel the needle rearwardly.

U.S. Pat. No. 4,838,869 discloses a head on its needle to establish a rim that is held in place by holding tabs. The tabs must be disengaged to permit the spring-loded needle to retract into the inner cylinder for storage.

Many prior syringe and retractable needle combinations have also been proposed which use manual retrieval of the needle by the forward end of the plunger, whereupon the plunger is retracted and pulls the needle into the body of the syringe. These double action syringe and needle combinations have not been widely used. The reasons for this stem from the need for a two handed action being necessary on the part of the user to eliminate the risk of needle stick. Such techniques are generally prohibited by OSHA standards. The second manual step requires a person to grasp the outer body of the syringe and retract the needle against some resistance. This retraction could result in a slip on the part of the user and fouling of the needle against the user.

SUMMARY OF THE INVENTION

An object of the present invention is to simplify the structure necessary to create a one step one handed retractable needle and syringe combination. The invention uses and adapts the conventional syringe apparatus to provide a novel design that is unique adapted to provide practical manufacture and use. In addition, the user does not need to learn any procedure beyond what is necessary for conventional syringe and needle combinations.

The present retractable needle and syringe combination requires an extension of the stroke of the plunger to disengage the needle retractor from a forwardly located expanding collet. The collet expands and releases the spring biased needle retractor into the body of the syringe.

The instant design eliminates the necessity of side fluid ports and multiple internal seals associated with other syringes that utilize expanding collect concepts to secure the retract needle holder.

The instant design eliminates the necessity for an inner barrel to hold the cannula hub and retractable holder after they have been released by the collet. This is accomplished by use of a hollow plunger with a collapsible face that forces fluid out of the syringe but will accept the cannula, hub and holder when the plunger has opened the collet and the spring loaded needle assembly is permitted to retract.

The needle (cannula and hub) are of a conventional type and attach externally to the syringe via a screw engaged assembly. As stated above, the syringe includes a hollow plunger with a forward capped end and a syringe barrel. A total of one spring, two o-ring seals, and five plastic molded parts make up the specialized parts of the preferred embodiment. To the extent possible, the balance of the commonly used components, i.e., caps for needles and packaging for syringes, are all unmodified conventional off-the-shelf designs. However, the unique features of this invention provide substantial and non-obvious benefits over the prior art.

By virtue of the simplicity of componentry and use, the combination retractable needle and syringe of the present invention will be easily used, economically manufactured, and well adapted for mass use. Owing to these practical features, widespread use and disease prevention from the needle stick should be greatly reduced if not eliminated altogether.

BRIEF DESCRIPTION OF THE DRAWINGS

FIG. 1 is a partial sectional side view of a syringe according to the present invention;

FIG. 2 is a partial sectional side view of a syringe according to the present invention shown with the plunger in a forward position, a screw mounted needle according to the present invention is also shown;

FIG. 3 is a partial sectional side view of a combination syringe and needle according to the present invention shown in the retracted position;

DETAILED DESCRIPTION OF PREFERRED EMBODIMENT

Figure 4:
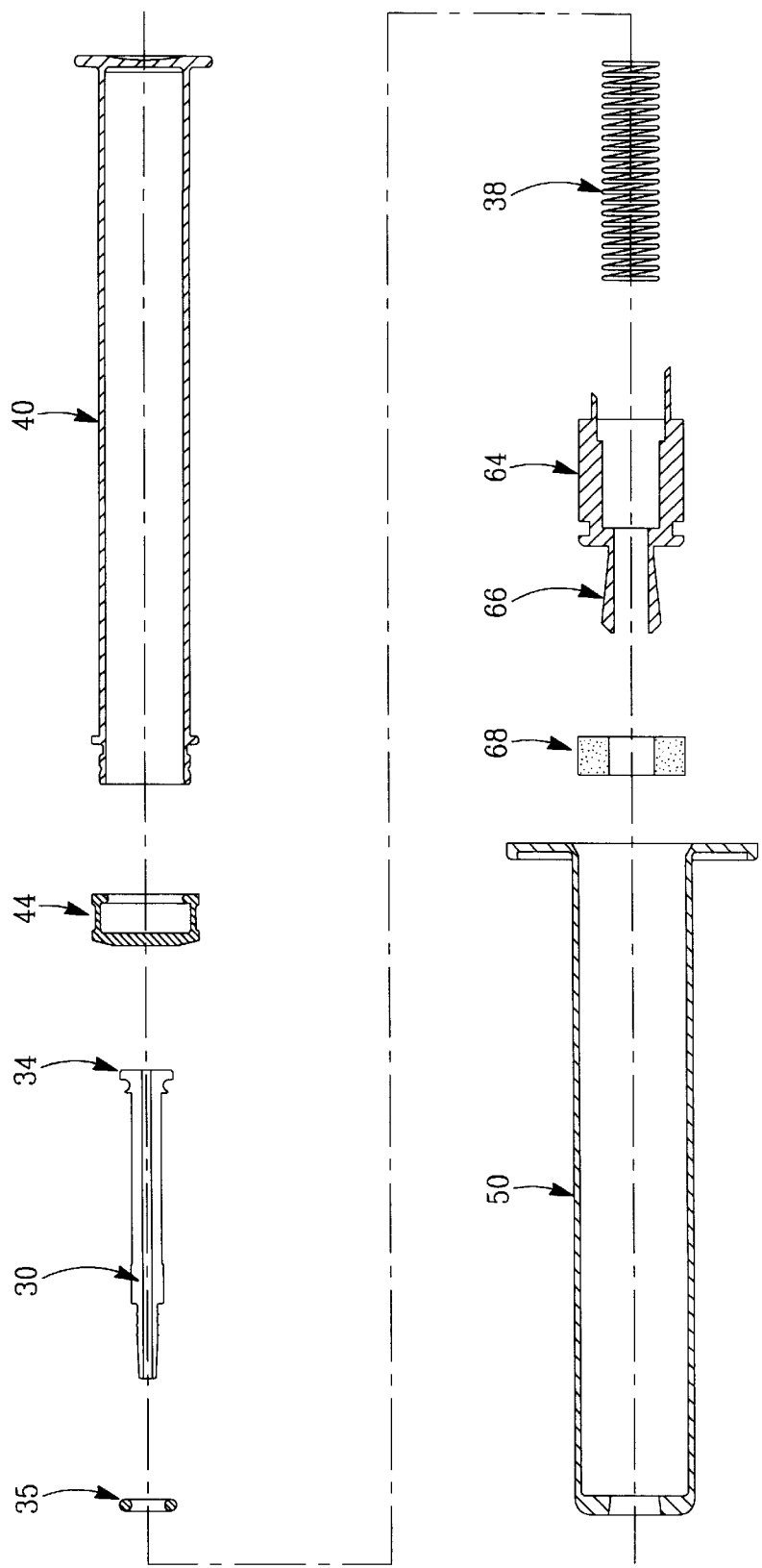
FIG. 4 is an exploded view of a syringe according to the present invention showing the assembly sequence of the component parts.
Figure 5:
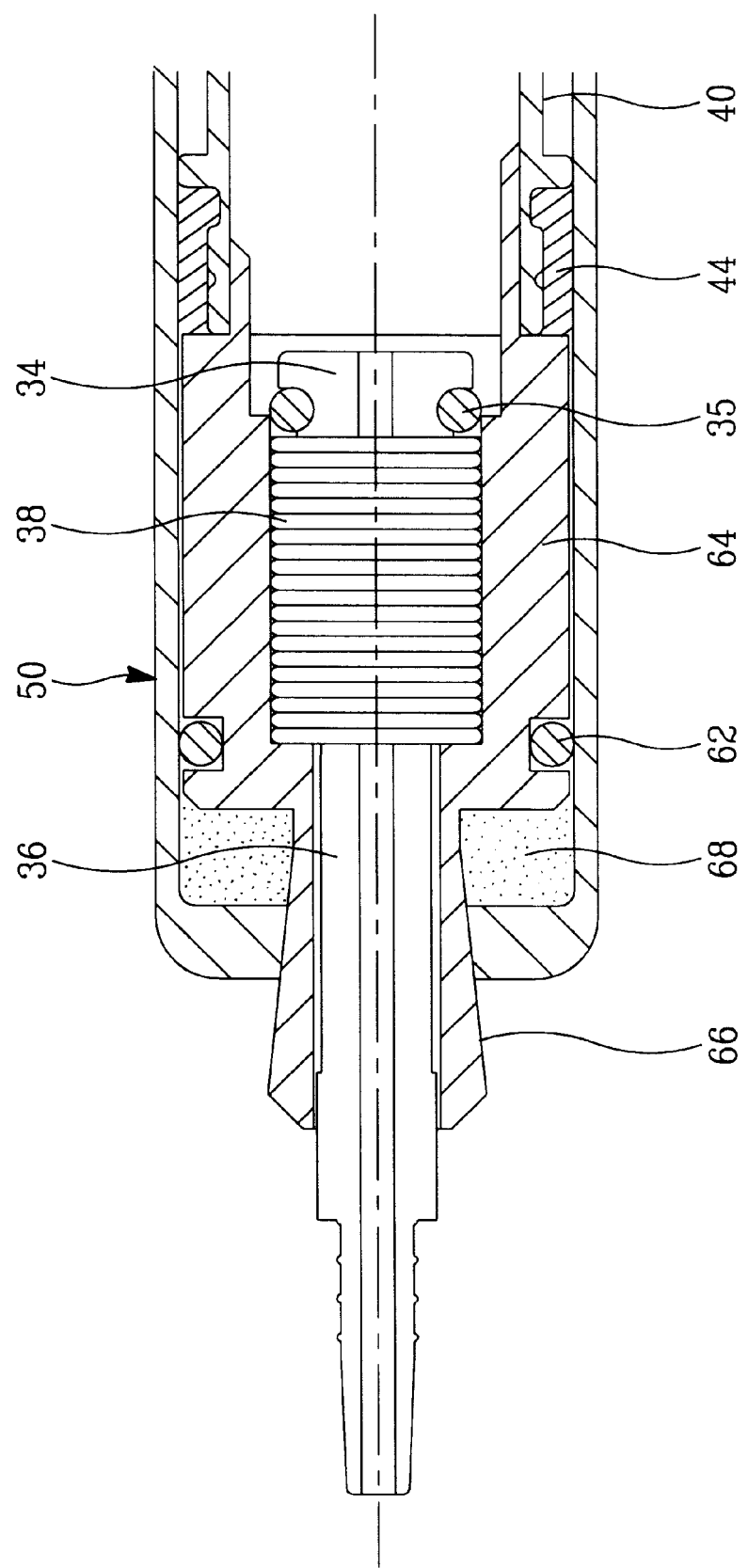
FIG. 5 is an enlarged partial sectional view of the forwarded end of an assembled syringe according to the present invention.

With reference to the drawing figures which form a part hereof, the following description is given. As shown in FIGS. 1–5, the invention is a combination syringe 20 and needle 10 device.

These parts are adaptable to utilize a needle assembly which can be utilized on a conventional syringe with a male connecting component. The syringe 20 device of the invention includes a hollow plunger 40 which cooperates with a needle retractor 30 to permit the needle 10 to retract into the plunger following use. The needle withdrawal action is accomplished by continuing the stroke of the plunger 40, following the emptying of the syringe by exerting additional pressure on the plunger the cap on the face of the plunger until the collapsible cap 44 collapses. Additional pressure then causes the needle retractor 30 to be released from the collet 66 and propelled by spring action into the body of the inner barrel of the plunger 40. The structure of the preferred embodiment that accomplishes the objectives of this invention will now be described.

The syringe 20 is made up of an outer barrel or tube 50. The collet has a base 64 receiving an o-ring seal element 62. The o-ring seal element 62 seals the base of the collet to the inner surface of the outer barrel 50. This creates a fluid containment chamber which can be pressurized by the introduction of the plunger 40 having a collapsible cap 44 into the containment chamber from the rearward end of the tube 50 of the syringe 20. The plunger has a tubular body 40 and an annular plunger end in the form of a collapsible cap 44. A collapsible cap 44 is placed on the forward face of the plunger. At the rearward end of the plunger a push element 46 is provided to engage a user's thumb.

The collet 66 has a slotted external funnel shape which creates a contacting and clamping external funnel effect for the collet as it is pressed through the opening located at the forward end of the outer tube 50. The collet is biased into a clamping or retracted position by a short collapsible foam ring or washer 68 which biases the collet base 64 rearwardly with respect to the outer tube 50.

Figure 6:
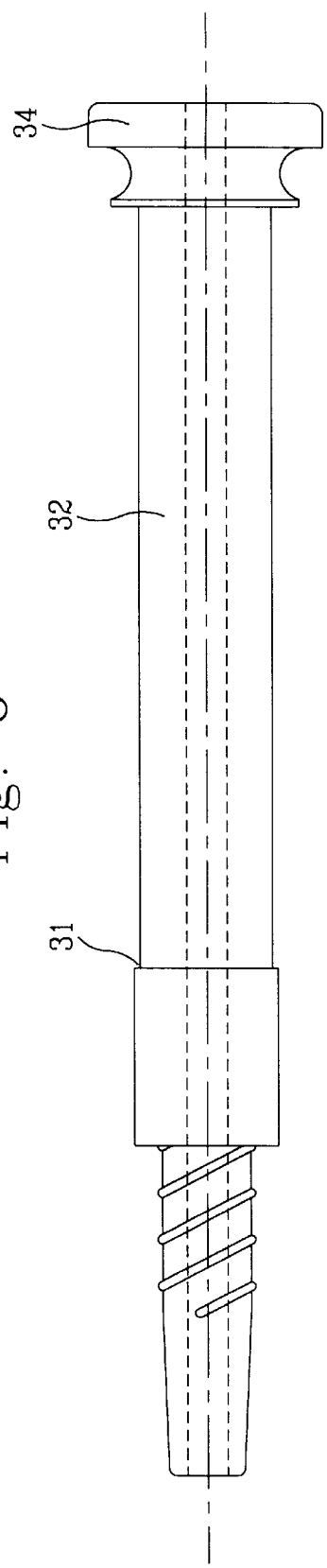
FIG. 6 is a plan view of the needle retractor of the present invention.
Figure 7:
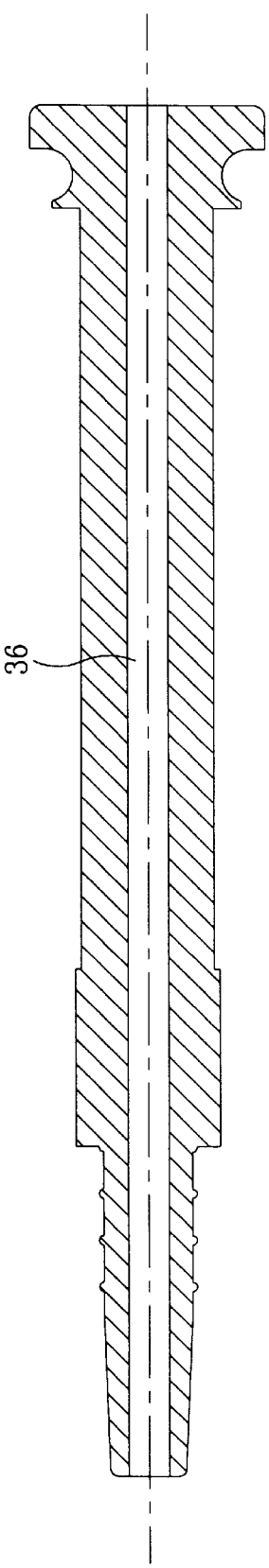
FIG. 7 is a sectional view of the needle retractor shown in FIG. 6.

The device further includes a retracting needle holder 30 shown in detail in FIGS. 6 and 7. The holder 30 is adapted to be inserted through the tubular body of the collet 60 from the rearward end thereof. The holder 30 includes a body portion 32 with an end cap 34 on the rearward end thereof and a fluid port 36 at the rearward end extending to the forward end thereof The retracting holder 30 passes fluid from the containment chamber upon pressurization thereof by the plunger 40 through the holder fluid port 36 into the needle 10. The holder is sealed to the inner surface of the collet base 64 by an o-ring seal 35.

Figure 8:
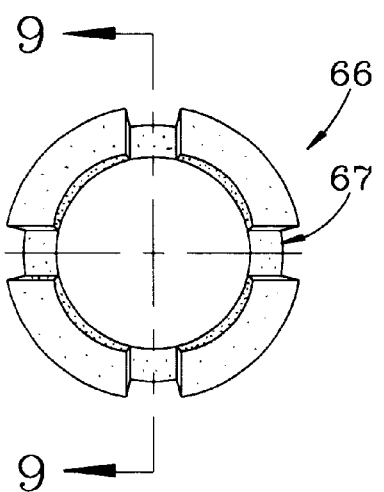
FIG. 8 is an end view of the expanding collet used in the present invention.
Figure 9:
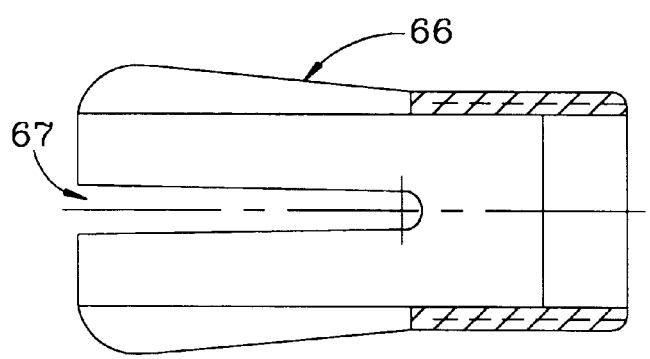
FIG. 9 is a cross sectional view of the collet shown in FIG. 8 along section IX—IX.

Details of the collet 60 and collet base 64 of this embodiment are shown in FIGS. 8 and 9. The collet includes slots 67 which allow for expansion and contraction of the collet as the exterior funnel shape of the collet is urged forward through the forward opening in the outer tube 50 of the syringe 20. When the collet 66 is urged rearwardly with respect to the outer tube 50 by a collapsible foam member 68, the collet forward end shrinks in diameter and clamps onto the exterior of the holder 30. It should be noted that this invention encompasses a variety of resilient members, i.e. a coil spring, a polymer collapsible o-ring, etc., that urge the collet in the rearward direction in the same manner as the foam member 68. This clamping and retention of the holder is helped by the trap edge 31 which is present on the exterior of the holder 30. The collet 66 clamps onto the holder just behind the trap edge 31. The trap edge 31 is shown as an annular element in this embodiment, however it can take on any shape which binds against the restricting edges of collet 66 and retains the holder 30 in the forward end of the collet 60.

The holder 30 is biased rearwardly by long spring 38 which pushes on the end cap 34 of the holder. To release the holder 30, the collet 66 is expanded by pushing the collet 66 forward by a push on the base of the collet forward by the forward end of the plunger. The forward end includes the collapsible cap 44 which is punctured by the tangs 65 provided on the rearward end of the collet base 64. When a user has dispensed the fluid by a full stroke on the plunger, the plunger is pushed past the full stroke position. The collapsible end cap is then ruptured and the plunger pushes against the collet base 60 which in turn pushes the collet 66 forward. By pushing forward, the collet 66 expands and the holder 30 disengages from the collet 66 and the holder 30 is propelled rearwardly into the tubular body of the plunger. The syringe 20 and needle 10 are then disabled with the needle trapped within the syringe as shown in FIG. 3.

The assembly sequence of the present invention is shown in FIG. 4. The plunger 40 and forward collapsible end cap 44 are assembled. The holder 30 and associated spring 38 and o-ring seal 35, are then inserted into the collet which is comprised of a collet base 60, seal 62, and collet 66. The o-ring seal 62 is placed on to the exterior of the collet base 60. The collet base 60 and collapsible single cell foam washer 68 are loaded into the outer tube 50, followed by the insertion of the assembled holder 30. The holder 30 is inserted until engagement with the collet occurs followed by the insertion of the assembled plunger. The entire syringe of the preferred embodiment includes five polymer plastic molded parts, namely the plunger, plunger cap, outer barrel, collet, and the holder, two o-ring seals, one spring and one collapsible single cell foam spacer. The seals can also be a polymer. This would enable the seals to be molded together with the respective collet and holder as desired. By virtue of the comparatively few number of parts and their simplicity in execution, the present syringe and retractable needle combination can be readily and economically manufactured.

The foregoing is a description of some of the preferred embodiments and best mode of the invention. Other versions of this invention can be created without departing from the spirit and scope of the invention which is limited only by the claims appended hereto.

I claim:

1. A syringe, comprising:

an outer barrel portion having a forward end and a rearward end;

a collet adapted for insertion into the rearward end of outer barrel, said collet having an expandable spreading portion on the forward end thereof, said forward end adapted to engage an opening in the forward end of said outer barrel, said opening constricting the collet as the collet is pulled rearwardly through said opening;

a sealed connection provided between said collet and said outer barrel so as to contain fluid in a fluid containment chamber within the interior of the outer barrel portion;

collapsible spacer positioned between the outer barrel and the collet so as to bias the collet base rearwardly with respect to the outer barrel;

a needle retractor element having a forward end adapted to receive a needle, said needle retractor having a tubular body and a fluid port contained therein, said needle retractor being inserted into the tubular body of the collet and engaged by said expandable collet, said fluid port located at the rearward end of the collet being fluid communication with the fluid containment chamber defined within the outer barrel;

spring means for biasing the needle retractor rearwardly, said spring means positioned between the collet and the needle retractor; and, a plunger element and collapsible cap adapted for insertion into the containment chamber for pressurizing any therein contained fluid and urging said fluid through said fluid port, located in the center of the rearward end of the collet, whereby, at the user's discretion, forward movement of said collet base with respect to the outer barrel releases the cap on the forward end of the plunger and releases the needle retractor element rearwardly into the hollow plunger.

2. A syringe as in claim 1, wherein said fluid port extends an entire length of said needle retractor.

3. A syringe as in claim 1, further comprising rupture tang projecting from said collet base, said rupture tangs adapted to penetrate said collapsible cap.

4. A syringe as in claim 1, further comprising:

a needle affixed to a hub member to form a needle assembly, said needle assembly connected to said forward end of the needle retractor element.

5. A syringe as in claim 4, further comprising:

screw attachment means for attaching the needle assembly to the forward end of the needle retractor.

6. A syringe as in claim 1, wherein:

said spring means comprises a coil spring.

7. A syringe as in claim 1, wherein:

said collapsible spacer comprises at least one of a single cell foam member, a polymer collapsible o-ring spacer, and a resilient spring.

8. A syringe as in claim 1, further comprising:

first discrete o-ring seal means for sealing the outer barrel portion to the collet base.

9. A syringe as in claim 8, wherein: the first discrete o-ring seal means compromises an o-ring type seal.

10. A syringe as in claim 1, wherein:

the expandable collet has funnel shaped exterior and includes slots in the sides thereof to enable expansion and contraction of a longitudinal passageway located within the collet.

* * * * *